United States Patent [19]

Ashida

[11] Patent Number: 4,611,013

[45] Date of Patent: Sep. 9, 1986

[54] CATALYSTS FOR THE PREPARATION OF CARBODIIMIDE FOAMS AND ELASTOMERS

[75] Inventor: Kaneyoshi Ashida, Detroit, Mich.

[73] Assignee: BP Chemicals Limited, London, England

[21] Appl. No.: 619,857

[22] Filed: Jun. 12, 1984

[51] Int. Cl.[4] .................... C08G 18/14; C08G 18/16; C07C 107/02

[52] U.S. Cl. .................... 521/105; 558/290; 521/901; 521/902; 528/52

[58] Field of Search .................... 521/105, 901, 902; 528/52; 260/462 R

[56] References Cited

U.S. PATENT DOCUMENTS

| | | | |
|---|---|---|---|
| 3,127,404 | 3/1964 | Mascioli | 521/105 |
| 3,639,234 | 2/1972 | Wixon et al. | 260/462 R |
| 3,772,357 | 11/1973 | Hamanaka | 260/462 R |
| 4,265,664 | 5/1981 | Saischek et al. | 260/462 R |
| 4,425,444 | 1/1984 | White | 521/105 |
| 4,530,938 | 7/1985 | White | 521/105 |
| 4,542,163 | 9/1985 | White | 521/105 |

*Primary Examiner*—Herbert S. Cockeram
*Attorney, Agent, or Firm*—Brooks Haidt Haffner & Delahunty

[57] ABSTRACT

New compounds which are salts of the formula $A^+ B^-$ where $A^+$ is a quaternary ammonium cation and $B^-$ is a tetrahedral boron-oxygen complex anion are prepared from boric acid by reaction with a hydroxyl compound and a quaternary ammonium hydroxide. The salts are used as catalysts to prepare carbodiimides and isocyanurates from isocyanates which can be in the form of foamed resins.

8 Claims, No Drawings

CATALYSTS FOR THE PREPARATION OF CARBODIIMIDE FOAMS AND ELASTOMERS

This invention relates to new salts containing a quaternary ammonium cation and a tetrahedral boron-oxygen complex as the anion, hereafter referred to as a boronium anion, to a process for their preparation and to their use as catalysts in the preparation of carbodiimides and isocyanurates.

Polycarbodiimides are well known in the art as thermally stable and substantially flame-retardant polymers. In recent years catalysts have been found which can greatly accelerate formation of the carbodiimide linkage by the condensation of isocyanate groups. A review on the preparation of carbodiimides from isocyanates appeared in Angewandte Chemie Internationale Edition, Vol.1, (1962), No.12, p 621 by W. Neumann and P. Fischer.

Among the compounds which have been previously described as carbodiimide-forming catalysts for example organophosphorus compounds, triazine compounds and organoarsine compounds.

For the trimerisation of isocyanates the use, as catalysts, of alkali metal salts of tetrahedral boron-oxygen complexes has been previously described for example, U.S. Pat. No. 3,635,848 describes the preparation of boronium ion-containing compounds, for example certain tetraalkoxy or tetraaryloxy borate coordination compounds such as

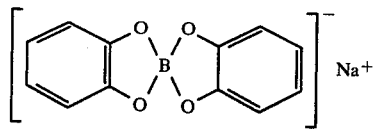

and

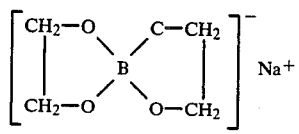

and their corresponding potassium, lithium, rubidium and caesium salts. These compounds are described as trimerisation catalysts for the preparation of isocyanurate structures from isocyanates.

U.S. Pat. No. 3,697,485 also describes the preparation of boronium ion-containing compounds derived from an orthoborate of a monohydric alcohol, 1,3 glycol or a monohydric phenol and an alkali metal alcoholate or phenolate salt. The compounds are described as catalysts for the polymerisation especially the trimersiation of isocyanates to form isocyanurates.

U.S. Pat. No. 3,127,404 describes the preparation of boronium ion-containing compounds in which the counter ion (cation) is derived from triethylene diamine (1,4, diaza (222) bicyclo octane). The compounds are described as polyurethane forming catalysts and it is suggested that they are dissociated by the exothermic heat of reaction to generate the free triethylene diamine catalyst.

It has now been found that quaternary ammonium boronium compounds are effective catalysts for the preparation of (i) carbodiimides by a condensation reaction to produce the carbodiimide and carbon dioxide and of (ii) isocyanurates by the trimersiation of isocyanates and that both reactions can be performed at room temperature i.e. about 20° C.

These catalysts can produce carbodiimide linkages not only from aromatic isocyanates but also from aliphatic isocyanates. In contrast, 1-phenyl-3-methyl-2-phospholene-1-oxide which is a representative prior art carbodiimide catalyst, does not produce aliphatic carbodiimides. Furthermore, synthesis of this catalyst is very complicated and the catalysts is therefore expensive.

Conveniently the four alkyl radicals constituting the quaternary ammonium cation are the same or different and contain from 1 to 20 carbon atoms.

Some examples of the quaternary ammonium cation include tetramethyl-ammonium, tetraethylammonium, cetyltrimethylammonium, and cetyldimethylethylammonium.

In the case of monohydric alcohols the complex acid can be prepared according to the following equation:

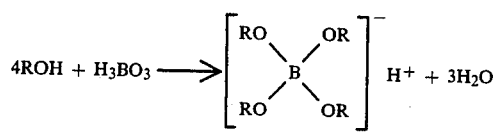

Most of the compound are slightly soluble in the common organic solvents, but more soluble in alcohols, tetrahydrofuran and other polar solvents. Slight excess of monohydric alcohol is used in the above equation, because the complex acid is soluble in the excess alcohol.

In the case of diols, dibidentate type coordination compounds are obtained as shown in the following equation:

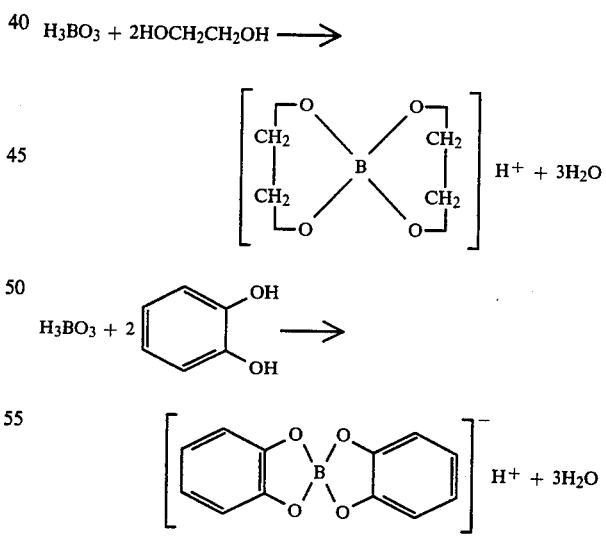

These bidentate derivatives are stable to hydrolysis, and therefore, they form quaternary ammonium salt quantitatively by the use of aqueous quaternary ammonium hydroxide without any hydrolysis of the boron complexes.

A mixture of a monohydric alcohol and a diol also can be used for preparing the boronium acids. An example of the hybrid complex has the following formula

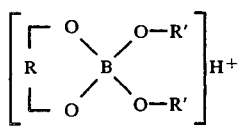

In the case of glycerine as the hydroxyl compound, the following complexes are obtained

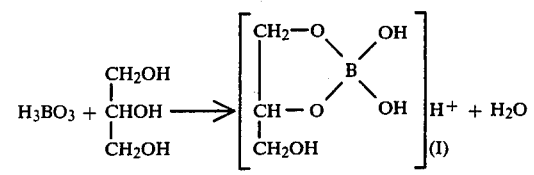

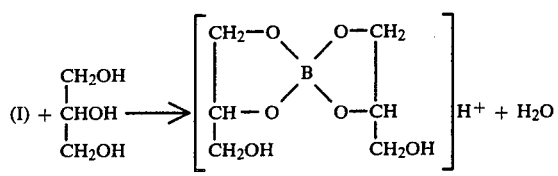

All of the tetrahedral boron-oxygen complex acids are strongly dissociated, and can form salts by adding a quaternary ammonium hydroxide.

The monohydroxyl compounds for the preparation of the tetrahedral boron-oxygen complex include monohydric alcohols and phenols. Examples of the monohydric alcohols are methyl alcohol, ethyl alcohol, 1-propanol, 2-propanol, n-butanol, sec-butanol, 1-hexanol, 2-ethyl 1-hexanol, 1-octanol, 2-octanol, 3-octanol, 4-octanol, cetyl alcohol, allyl alcohol, benzyl alcohol, phenoxyethyl alcohol etc. Examples of the phenols are phenol, O-cresol, m-cresol, p-cresol, 2,6-dimethylphenol,3,3-dimethylphenol,3,5-dimethylphenol, etc.

The dihydroxyl compounds for the preparation of tetrahedral boron-oxygen complex include di- and polyhydric alcohols, catechol and salicylic acid. Examples of dihydric alcohols include alkylene glycols and oxyalkylene glycols, such as ethylene glycol, 1,2-propanediol, 1,3-propanediol, 1,4-butanediol, 1,5-hexanediol, 1,6-hexanediol, 2,5-hexanediol, 1,8-octanediol, polyoxyethylene glycols, polyoxypropylene glycols, polyester polyol, diethylene glycol, triethylene glycol, tetraethylene glycol, etc.

Low molecular weight diols can be bidentate for the boron complex, e.g., ethylene glycol, 1,2-and 1,3 propanols, triethylene glycol, etc.

High molecular weight diols cannot be a bidentate because they cannot form a stable ring, and therefore, they form the other type of complex, i.e.,

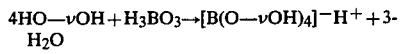

Such high molecular weight diol-based boron complexes can be a carbodiimide catalyst, however, its catalytic activity is lower than the low molecular weight diol-based complexes.

Examples of trihydric alcohols are glycerine, trimethylolpropane, and 1,2,6-hexanetriol.

Preparation of tetrahedral boron-oxygen complexes can be made by the two step method or by the one step method.

The two step method comprises (a) the reaction of boric acid with a mono- or poly-hydric copound by removing the byproduct water. The removal of the byproduct water can be effected by azeotropic distillation and/or distillation at atmospheric pressure followed by reduced pressure and (b) the neutralization of the complex acid with a quaternary ammonium hydroxide which was followed by removal of by product water.

In the case of bidentate type of the boron complex, a one step method can be applied because the complex is hydrolysis-resistant. The method comprises mixing boric acid into a diol, and adding a quaternary ammonium hydroxide to the mixture. The reaction is completed by removing the byproduct water by azeotropic distillation or atmospheric and/or reduced pressure distillation.

Polycarbodiimides are highly thermally stable and are substantially non-combustible. However, due to the lack of an active catalyst and its high cost, carbodiimide-based polymers have not been commercialised. This invention may provide a possible chance of the commercialisation. The new catalyst of the present invention is very active, and therefore, polycarbodiimides are obtained not only from aromatic polyisocyanate but also from aliphatic isocyanates as well as isocyanate-terminated adducts or prepolymers.

The organic polyisocyanates to be used in the present invention are defined as organic compounds having at least two isocyanate radicals.

The organic polyisocyanates inlude aromatic diisocyanates, aliphatic diisocyanates, isocyanate-terminated adducts and prepolymers of organic polyisocyanates.

Some examples of aromatic diisocyanates include 2,4-tolylene diisocyanate, 2,6-tolylene diisocyanate, 80/20 mixture of 2,4- and 2,6-tolylene diisocyanate, 4,4'-diphenylmethane diisocyanate, p-phenylene diisocyanate, m-phenylene diisocyanate, 2,5-naphthylene diisocyanate, 3,3'-dimethoxy-4,4'-diphenyl diisocyanate and a polymeric isocyanate of the general formula

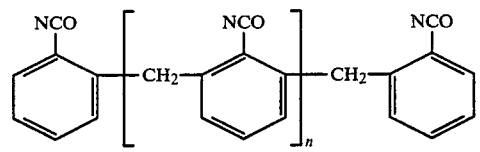

where n is greater than 0 and less than 10.

Some examples of aliphatic diisocyanates include tetramethylene diisocyanate, pentamethylene diisocyanate, hexamethylene diisocyanate, decamethylene diisocyanate, hydrogenated 4,4'-diphenylmethane diisocyanate, 1,3-bis(isocyanatomethyl)cyclohexane or hydrogenated xylylene diisocyanate, 3-isocyanatomethyl-3,5,5-trimethylcyclohexyl isocyanate or isophorone diisocyanate.

The term "Isocyanate-terminated adducts" in the present specification refers to reaction products of low molecular weight polyols, e.g. diols and triols, with organic polyisocyanates, in an NCO/OH equivalent ratio of at least 2.0/1.0. Some of the examples are a reaction product of hexamethylene diisocyanate with trimethylolpropane, a reaction product of 2,4-tolylene diisocyanate with 1,2,6-hexanetriol.

The term "Isocyanate-terminated prepolymers" in the present specification refers to reaction products of organic polyisocyanate with a polyhydroxyl compound having at least two hydroxyl groups and a molecular weight of at least 300. Some examples are polyoxyethylene glycols and polyoxypropylene glycols, and polyester polyols such as polycaprolactones, in an NCO/OH equivalent ratio of at least 2.0/1.0. The molecular weight of the polyols can be in a range of about 300 to 6000.

A variety of carbodiimide linkage-containing polymers, e.g., flexible and rigid forms, elastomers, coatings, etc can be prepared by using the catalyst according to the present invention.

Some of the catalysts of the present invention act simultaneously as carbodiimide catalyst and trimerisation catalyst. Therefore, the carbodiimide linkage formation results in chain extension, and trimerisation or isocyanurate linkage formation results in the cross linking of the resultant polymers. The concerted reactions i.e., chain extension and cross-linking, occur simultaneously and are very advantageous in the foam preparation.

For example, single use of an isocyanate-terminated prepolymer results in flexible foams, and single use of organic polyisocyanate and/or short chain adducts or prepolymers results in rigid foams.

In the case of foam preparation, a surfactant is preferably used, but the use of blowing agent is not always necessary, because carbodiimide-linkage formation reaction simultaneously generates carbon dioxide gas which acts as a blowing agent.

If lower density foams are requested, however, an inert and low boiling point solvent can be added in the foaming component. Some of the examples of inert solvents are trichloromonofluoromethane, hexane, benzene, methylene chloride, trichloroethane etc.

If higher density foams are desired, a polyol is added as a modifier into the foaming component. The polyol can be either a polyether polyol or a polyester polyol. Such urethane-modified carbodiimide foams result in increased density and reduced thermal stability.

The preparation of urethane-modified carbodiimide foams can be obtained by the co-use of a polyol and a urethane-forming catalyst, e.g., a tertiary amine, and/or a tin catalyst such as stannous octoate, dibutyltin dilaurate etc.

Carbodiimide linkage-containing coatings can be prepared by using the catalyst of the present invention in a solvent from which carbon dioxide gas is separated and a film results. For industrial applications, a two component coating system, e.g., catalyst component and polyisocyanate component, can be preferably used.

The invention is illustrated by the following examples.

EXAMPLE 1

Preparation of Tetraethylammonium salt of triethyleneglycol-based tetrahedral boron-oxygen complex:

Two moles (300 grams) of triethylene glycol and 0.50 mole (30.9 grams) boric acid were charged into a one-liter, three necked flask equipped with a stirrer, a thermometer and a condenser. The reaction mixture was heated at 110° to 120° C. and the byproduct water was distilled off at atmospheric pressure, followed by vacuum distillation to remove remaining traces of water.

Into a resultant product, a 20 weight percent aqueous solution of tetraethylammonium hydroxide was added until neutral as shown by phenolphthalein indicator. Then, water was removed by reduced pressure distillation followed by vacuum distillation. The salt obtained was a viscous liquid.

EXAMPLE 2

Preparation of foamed resin

The salt obtained according to Example 1 in an amount of 0.5 ml was mixed with TDI(80/20 isomer ratio) in an amount of 5.0 ml in a test tube, and heated in an oil bath at 70° C. for about one minute. A vigorous gas generation and solidification took place and a rigid foamed product resulted.

The foamed product showed an infrared absorption at 2130 cm$^{-1}$ which shows the existence of carbodiimide linkage and at 1700 cm$^{-1}$ which suggest the existence of carbodiimide dimer, trimer or isocyanurate linkages.

The gas generated was shown to be carbon dioxide by means of the formation of barium carbonate from barium hydroxide.

EXAMPLE 3

Preparation of cetyltrimethylammonium salt of triethyleneglycol-based tetrahedral boron-oxygen complex:

$[B(OC_2H_4OC_2H_4OC_2H_4OH)_4]^-[N(C_{16}H_{33})(CH_3)_3]^+$

Cetyltrimethylammonium hydroxide aqueous solution was prepared by passing its bromide solution over a strong base type anion exchange resin (Diaion PA-308, Mitsubishi Chemical Ind. Ltd. Japan) in the OH form of quaternary ammonium type.

The quaternary ammonium hydroxide aqueous solution was used for neutralising the tetrahedral boron-oxygen complex obtained by Example 1. The by-product water was removed by an atmospheric distillation followed by vacuum distillation.

The salt obtained was a viscous liquid.

EXAMPLE 4

Preparation of Foamed Resin

The complex obtained according to Example 3 was dissolved in diethylene glycol and cellosolve acetate respectively to make a 25% solid solution. The salt was completely soluble in the former, and partially soluble in the latters.

The catalyst solution in an amount of 0.5 ml and TDI (80/20 isomer ratio) in an amount of 5.0 ml were mixed in a test tube. After about 2 minutes standing at room temperature, a vigorous exotherm reaction and gas generation took place, and a rigid foamed resin resulted. The product had an IR absorption band at 2130 cm$^{-1}$ and 1700 cm$^{-1}$.

EXAMPLE 5

Preparation of tetramethylammonium tetrabutoxyborate:

Boric acid in an amount of 36.6 grams and n-butyl alcohol in an amount of 235 grams were charged in a three-necked flask, and azeotropic distillation was applied.

Into the solution obtained, stoichiometric amount of trimethylammonium hydroxide was added and vacuum distillation was applied. The resultant salt was solid and was soluble in cellosolve acetate, dimethylformamide and diethylene glycol.

EXAMPLE 6

Preparation of foamed product

Into 5.0 ml of TDI (80/20 isomer ratio), about 0.5 ml of the salt obtained according to Example 5 was mixed in a test tube, and it was dipped and shaked in an oil bath kept at 80° C. After few seconds, gas generation begun and a rigid foam mass resulted.

EXAMPLE 7

Preparation of tetraethylammonium salt of catechol tetraborate complex.

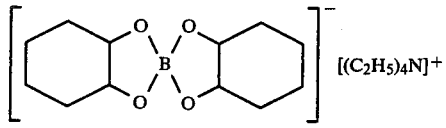

Twenty two grams (0.2 mole) of catechol, 6.18 gram (0.10 mole) of boric acid and 73.5 grams (0.10 mole) of tetraethylammonium hydroxide as 20% aqueous solution were charged into a 3-necked flask equipped with outlet and inlet tubes which were connected to a separation tower of azeotropic mixture. The separation tower was installed according to the paper: Kaneyoshi Ashida, "Suspension Polycondensation in Azeotropic System", The Chemistry of High polymer (Japan), Volume 11, pages 164–168 (1954).

Into the flask, about 250 ml of carbon tetrachloride was charged and the flask was heated for azeotropic distillation of byproduct water. It took about 24 hours until no water distilled out. After standing overnight at room temperature, crystals were separated from carbon tetrachloride. The crystals had violet colour and a melting point of 85° C. The crystals was soluble in cyclohexanone, tetrahydrofuran, alcohols, and insoluble in benzene, toluene, carbon tetrachloride.

A solution, e.g., cyclohexanone solution had red wine colour.

EXAMPLE 8

Preparation of Foamed Mass

The complex salt obtained by the method of Example 7 was dissolved in diethylene glycol and methanol respectively to obtain a saturated solution.

0.5 ml of one of the saturated solutions and 5.0 ml of TDI (80/20 isomer ratio) were mixed in a test tube, and immersed in an oil bath kept at 80° C. overnight.

The resultant foam had IR scans showning the carbodiimide absorption at 2130 cm$^{-1}$.

Preparation of isocyanurate-containing flexible foams

EXAMPLE 9

Fifty grams of Niax 11-34 (OH No. 35.5 mgKOH/g, primary hydroxyl-capped polyol, Union Carbide Corp), 1.25 grams of water, 0.50 gram of silicone surfactant SC-162 (BP Chemicals Ltd.), and 1.0 gram of a boronium catalyst prepared by the reaction of 1.0 mole of boric acid, 6.0 mole of triethylene glycol and 1.0 mole of tetraethylammonium hydroxide, and 20.9 grams of TDI were mixed and stirred vigorously to make a foam.

The cream time and rise time observed were 65 seconds and 280 seconds, respectively. The foam density was found to be 69.6 kg/m$^3$. By using the same formulation except the use of increased amount of the same catalyst, i.e. 2.0 grams, the resultant foam had a density of 56.2 kg/m$^3$.

EXAMPLES 10-13

The same formulation as in Example 9 was used except the catalyst combination shown below in place of the single use of the boronium complex. The catalyst combination employed and the foams obtained were as follows:

| Example No. | 10 | 11 | 12 | 13 |
|---|---|---|---|---|
| boronium catalyst, g | 1.0 | 2.0 | 1.0 | 1.0 |
| Niax Catalyst A-1, g | 0.07 | 0.15 | 0 | 0 |
| Dabco 33LV, g | 0 | 0 | 0.07 | 0 |
| Triethylamine, g | 0 | 0 | 0 | 0.07 |
| Cream Time, sec | 25 | 18 | 45 | 43 |
| Rise Time, sec. | 190 | 180 | 250 | 240 |
| Foam Density, kg/m$^3$ | 57.3 | 37.2 | 37.9 | 43.2 |

EXAMPLE 14

Ten grams of isocyanate-terminated prepolymer (6.7% NCO) prepared by the reaction of Pluracol 1010 (polyoxypropylene diol having a molecular weight of 1000, BASF Wyandotte Corp.) and TDI (80/20 isomer ratio), and 1.0 gram of a boronium catalyst prepared according to the procedure described in Example 9, were mixed in a test tube which was immersed in an oil bath heated at 80° C. During the heating, considerable gas generated, and after 5 minutes a foamed elastomer resulted.

EXAMPLE 15

Five grams of isocyanate 143L and one gram of boronium catalyst prepared in Example 9 were charged into a test tube, and heated by immersion in a oil bath kept at 100 degrees centigrade with stirring by a glass rod. After 2 minutes the reaction mass solidified.

EXAMPLE 16

Five grams of hexamethylene diisocyanate and one gram of a boronium catlyst prepared according to Example 9 were reacted in the same manner as in Example 15. After 2 to 3 minutes, a considerable amount of gas was generated and a foamed mass resulted.

EXAMPLE 17

An isocyanate-terminated urethane prepolymer prepared according to the procedure in Example 14 in an amount of 10 grams, boronium catalyst prepared according to Example 9 in an amount of one gram, and Cellosolve acetate in an amount of 5 mili-liters were mixed and coated on an aluminum foil and kept in an oven heated at 100 degrees centigrade. A transparent, flexible film was obtained.

EXAMPLE 18

A urethane-carbodiimide-modified isocyanurate foam was prepared according to the following conditions:

ten grams of ethylene glycol
20 grams of trichloromonofluoromethane, 2.0 grams of silicone surfactant SR 242 (BPCL Polyurax Silicone surfactant
6.0 grams of boronium catalyst prepared according to Example 9
1.0 gram of tin catalyst T-9 (M and T Co.)

were mixed to make a premix. Into the premix, 100 grams of PAPI 135 (polymeric isocyanate, Upjohn Compnay) were mixed under vigorous stirring. The cream time and rise time observed were 20 seconds and 68 seconds respectively. The density of the foam obtained was 38.9 kg/cubic meter.

The butler flammability (ASTM D3014-76) data of the foam was 78 percent weight retention. The infra-red spectra of the foam showed absorption bands for isocyanurate, urethane and carbodiimide linkages.

I claim:

1. A process for the preparation of a polyurethane containing carbodimide and/or isocyanurate structures which process comprises reacting an organic polyisocyanate with a compound containing at least two active hydrogen containing groups group in the presence, as catalyst, of an effective amount of a boronium salt containing a quaternary ammonium cation.

2. A process as claimed in claim 1 for the preparation of a foamed polyurethane wherein the process is effected in the presence of a blowing agent.

3. A process as claimed in claim 1 wherein the process is effected in the presence of a urethane-forming catalyst.

4. A process as claimed in claim 1 wherein the process is effected in the presence of a surfactant.

5. A process as claimed in claim 1 wherein the polyisocyanate is an isocyanate terminated prepolymer obtained by the reaction of an organic polyisocyanate with a compound having at least 2 active hydrogen atoms.

6. A process for preparing a compound containing carbodiimide and/or isocyanurate structures which process comprises condensing an organic poly-isocyanate in the presence as catalyst of an effective amount of boronium salt containing a quaternary ammonium cation and which salt has one of the following general formulae:

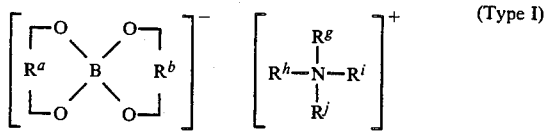 (Type I)

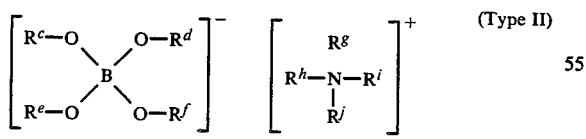 (Type II)

and

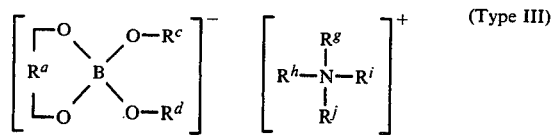 (Type III)

where
$R^a$ and $R^b$: are the same or different divalent organic groups containing from 2 to 8 carbon atoms;
$R^c$, $R^d$, $R^e$ and $R^f$: are the same or different monovalent-organic groups having 1 to 20 carbon atoms
$R^g$, $R^h$, $R^i$ and $R^j$: are each a monovalent organic group having 1 to 20 atoms.

7. A process for the preparation of a foamed resin containing carbodimide and optionally isocyanurate structures which process comprises condensing an organic polyisocyanate in the presence, as catalyst, of an effective amount of a boronium salt of claim 6 containing a quaternary ammonium cation, the foaming action being effected by carbon dioxide gas generated in the reaction.

8. A process for the preparation of a film which comprises coating a substrate with a solution of an isocyanate terminated pre-polymer in the presence of an effective amount of a boronium catalyst which is a boronium salt containing a quaternary ammonium cation and which salt has one of the following general formulae:

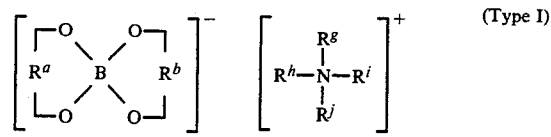 (Type I)

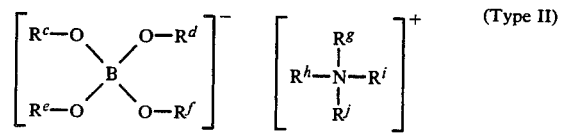 (Type II)

and

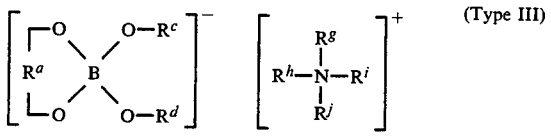 (Type III)

where
$R^a$ and $R^b$: are the same or different divalent organic groups containing from 2 to 8 carbon atoms;
$R^c$, $R^d$, $R^e$ and $R^f$: are the same or different monovalent-organic groups having 1 to 20 carbon atoms;
$R^g$, $R^h$, $R^i$ and $R^j$: are each a monovalent organic group having 1 to 20 atoms
and allowing a cured film to form.

* * * * *